US008563317B2

(12) United States Patent
Grossman et al.

(10) Patent No.: US 8,563,317 B2
(45) Date of Patent: Oct. 22, 2013

(54) APPARATUS FOR DETECTING GAMMA HYDROXYBUTYRATE, KETAMINES AND RELATED DRUGS IN BEVERAGES

(75) Inventors: Stanley Irwin Grossman, London (GB); James Gordon Campbell, Chaddesden (GB); Christian James Loane, Lesmurdie (AU)

(73) Assignee: Bloomsbury Innovations Ltd., London (GB)

( * ) Notice: Subject to any disclaimer, the term of this patent is extended or adjusted under 35 U.S.C. 154(b) by 1052 days.

(21) Appl. No.: 10/598,823

(22) PCT Filed: Dec. 16, 2004

(86) PCT No.: PCT/GB2004/005271
§ 371 (c)(1),
(2), (4) Date: Jun. 9, 2009

(87) PCT Pub. No.: WO2005/088297
PCT Pub. Date: Sep. 22, 2005

(65) Prior Publication Data
US 2011/0165687 A1 Jul. 7, 2011

(30) Foreign Application Priority Data
Mar. 12, 2004 (GB) .................................. 0405648.7

(51) Int. Cl.
*G01N 31/22* (2006.01)
*G01N 31/00* (2006.01)

(52) U.S. Cl.
USPC ................... 436/20; 435/7.9; 435/19; 435/26

(58) Field of Classification Search
USPC .................. 436/20; 435/7.9, 26, 19
See application file for complete search history.

(56) References Cited

U.S. PATENT DOCUMENTS

| 3,915,639 | A | * | 10/1975 | Friedenberg | .................... 436/98 |
| 3,955,926 | A | | 5/1976 | Fischer | |
| 4,187,076 | A | | 2/1980 | Elsohly et al. | |
| 4,810,596 | A | * | 3/1989 | Ludwig | .......................... 429/415 |
| 6,372,515 | B1 | | 4/2002 | Casterlin et al. | |
| 6,617,123 | B1 | * | 9/2003 | Smith | ............................. 435/19 |
| 2003/0026731 | A1 | | 2/2003 | Peter | |

FOREIGN PATENT DOCUMENTS

| GB | 2053680 | | 2/1981 |
| GB | 2377016 | A1 | 12/2002 |
| GB | 2383130 | A | 6/2003 |
| WO | WO 94/06940 | A1 | 3/1994 |
| WO | WO 96/27795 | A1 | 9/1996 |
| WO | WO 00/05579 | A1 | 3/2000 |
| WO | WO 00/63697 | A1 | 10/2000 |
| WO | WO 02/056019 | A1 | 7/2002 |
| WO | WO 03/021254 | A2 | 3/2003 |

OTHER PUBLICATIONS

Bonicamp et al., Method for Confirming the PResence of MEthaquaione on Thin-Layer Chromatographic Media.(1981). Clinical Chemistry. 27:2 359-360.*
Sigma Aldrich, definition of Dragendorff's Reagent.*
Abbreviated Examination Report under Section 18(3) dated Oct. 2, 2007.
Sharma et al., Planar Chromatography of Some Metal-EDTA Complexes on Silica Gel G Layers, J Chromat Sci, 1995, pp. 463-466, vol. 33.
Extended European Search Report and Opinion dated May 18, 2012 in related Application No. 11171404, 5 pages.

* cited by examiner

*Primary Examiner* — Krishnan S Menon
*Assistant Examiner* — Rebecca M Fritchman
(74) *Attorney, Agent, or Firm* — Dentons US LLP

(57) ABSTRACT

Apparatus for detecting the presence of foreign substances in a beverage. The apparatus for detecting the presence of Gamma-hydroxybutyrate or other drugs in a beverage comprises apparatus wherein cobalt nitrate, oxammonium chloride/ferric chloride, oxammonium sulphate/ferric chloride, 5% ferric chloride, saturated potassium dichromate, toluene/cobalt thiocyanate, chromium (IV) oxide/sulphuric acid carbodiimide salts in combination with oxammonium salts and ferric chloride, or lacmoid is supported on a substrate. The apparatus for detecting the presence of ketamines or other drugs in a beverage comprises apparatus wherein modified-Dragendorff Reagent is supported on a substrate.

18 Claims, No Drawings

APPARATUS FOR DETECTING GAMMA HYDROXYBUTYRATE, KETAMINES AND RELATED DRUGS IN BEVERAGES

CROSS-REFERENCES TO RELATED APPLICATIONS

This application is a national of PCT application PCT/GB2004/005271 filed on Dec. 16, 2004, which claims priority from British patent application 0405648.7 filed on Mar. 12, 2004, each of which is incorporated herein by reference in its entirety.

The present invention relates to apparatus for detecting the presence of foreign substances in a beverage. More particularly it relates to apparatus for detecting gamma-hydroxybutyrate and apparatus for detecting the presence of ketamine.

It has been known for many years for perpetrators wishing to cause harm to a victim to add a drug to the victim's beverage to alter the victim's behaviour or to incapacitate them totally. For example, alcohol may be added to a non-alcoholic drink or drugs may be added to either an alcoholic or non-alcoholic drink. When the victim has drunk the beverage, their mood may be altered, or they may become totally incapacitated. While the victim is suffering from the effect of the drug the perpetrator may take advantage of the victim. In its mildest form, the victim's behaviour may simply be the source of amusement. Whilst this may be the perpetrator's intent, the action can have more serious consequences since the drug dose is generally unknown, as is the effect of the combination of the drug with alcohol. Further the drug may have deleterious effects on any medical condition that the victim may have or may have an adverse interaction with any other medication that the victim may be taking. Unfortunately, there is usually a more sinister intent such as robbery, rape or even murder.

Drugs currently commonly used include alcohol, drugs from the benzodiazepine family, gamma hydroxybutyrate, 3,4-methylenedioxy-N-methylamphetamine (also known as MDMA or Ecstasy), ketamines, cannabis and the like. Recent studies suggest that there are at least two hundred drugs available legally or illegally which could be secretly applied to beverages for the purpose of disabling or incapacitating the victim.

Benzodiazepines such as flunitrazepam and which may be sold under the trade name Rohypnol, have become to be known as the "date rape" drug because of its misuse as an additive to beverages to cause the victim to loose inhibition, to become willing to any suggestion and since it causes antero-grade amnesia, means that the victim is unable to remember the events that occur under the influence of the drug. It is therefore commonly used to enable the perpetrator to obtain sex from the victim.

In an attempt to overcome this problem, the manufacturers of Rohypnol have added a blue dye to the prescription tablets to prevent them being added to drinks without the user's knowledge. However, there are still illicit forms of flunitrazepam available which are not coloured. Further other drugs such as gamma-hydroxybutyrate and ketamines can produce similar effects.

Gamma-hydroxybutyrate is a banned dietary supplement. While it does have legitimate uses such as in the treatment of depression and in the research into sleep disorders, opiate dependency and alcohol withdrawal, its effects means that it is misused.

Ketamine (2,2-chloropheyl-2-methylaminocyclohexone) is used as a paediatric or animal tranquilizer and when misused can induce a so-called spiritual feeling with a catatonic state and flashbacks.

The dosage of the drugs required to have a sedative effect varies, not only with drug type, but also with the method of manufacture used, the interaction with co-ingested substances and the physiology of the victim.

Drug rape usually goes unchecked since the victims are unable to remember the events or details and therefore are unreliable witnesses in any legal action. Even if the victim can remember some details or have suspicions they are often unwilling to come forward.

It is therefore desirable to provide a testing means which will enable users to test their beverage to establish whether it is safe to drink. The benefits of this system include that the user knows that he or she is safe. A further benefit of a testing method is that where the presence of a drug is detected, there is a possibility that the perpetrator may be identified. Any such device could also be used by authorities to screen drinks at the scene of an alleged offence.

Whilst there are a variety of established technologies available for testing for drugs, these are generally based on laboratory or clinical tests and are therefore not suitable for use by the average consumer. They are also usually time consuming and expensive to run and require the use of clean rooms and for strict protocols to be observed. In addition, many of these systems are not able to function in the presence of an acid or alcohol and therefore have limited use in testing for drugs in beverages. These known tests also generally are only able to test for one drug at a time and require resetting and recalibrating for the next drug to be tested.

Various proposals have been made to provide test apparatus which can be used at the site and time of consumption of the beverage. However, many of these are deemed unsuitable due to the lack of sensitivity and specificity and their incompatibility with some beverages.

US 2003/044989 describes an apparatus which can be used by an individual to detect qualitatively the presence of elicit substances in beverages. The test comprises a solid porous substrate with embedded indicators. The indicators are for the presence of GHB and ketamines. The indicators suggested are Zimmermann's reagent, platinum/potassium iodide, bromo-cresol purple and cobalt thiocyanate. However, the level of sensitivity is unacceptably low.

An alternative arrangement is described in US 2001/046710 in which a chemically treated carrier, which has been soaked with a solution that undergoes a visual colour change when in contact with gamma-hydroxybutyrate, and allowed to dry. The described reagent is one or more of cuprous chloride, copper acetate, tannic acid, ammonium nitrate, ferric ammonium sulphate and ferric chloride. However, again the level of sensitivity may not be as high as would be desired.

Whilst these arrangements go some way to providing a suitable solution to the desirability of providing a test which can be used at the point of consumption, it is still desirable to provide alternative, and preferably improved, arrangements which enable the victim to test for gamma-hydroxybutyrate or ketamines at the desired level of sensitivity.

Thus according to the present invention there is provided apparatus for detecting the presence of gamma-hydroxybutyrate or other drugs in a beverage wherein the apparatus comprises cobalt nitrate, oxammonium chloride/ferric chloride, oxammonium sulphate/ferric chloride, 5% ferric chloride, saturated potassium dichromate, toluene/cobalt thiocyanate, chromium (IV) oxide/sulphuric acid carbodiimide salts in combination with oxammonium salts and ferric chloride, or lacmoid supported on a substrate.

The apparatus preferably comprises lacmoid, which is preferably in the form of Loane's Reagent, supported on the substrate. In one arrangement of the present invention, the Loane's Reagent is buffered with an acid such as hydrochloric acid.

The lacmoid may be impregnated into the substrate. Impregnation may be in a polar solvent. Suitable polar solvents include acetone, methanol and water.

Where gamma-hydroxybutyrate is present the substrate will turn blue when it is brought into contact with the drink. The apparatus of the present invention offers an improved test for detecting gamma-hydroxybutyrate. For example, it can detect an equivalent of 200 mg of clandestine gamma-hydroxybutyrate material in most standard 250 ml beverages.

In a second embodiment of the present invention, there is provided apparatus for detecting the presence of ketamines or other drugs in a beverage wherein a modified-Dragendorff Reagent is supported on a substrate.

The modified-Dragendorff Reagent preferably includes an acidic salt to reduce the blackening effect encountered with aqueous solutions due to the precipitation of bismuth salts. Any suitable acidic salt may be used. Suitable salts include tartaric acid, oxalic acid, sodium bisulphate and citric acid.

The apparatus of this embodiment of the present invention produces an orange, pink or orange-pink colour in the presence of secondary amines including ketamine.

The apparatus of this embodiment can also be used to test for other drugs including benzodiazepines. Where a drink has been spiked with benzodiazepines, blackened speckles from the tablet bulking agents and tiny red/orange intense speckles due to the presence of the active benzodiazepine constituent are noted.

The substrate for both embodiments may be produced from any suitable material. Suitable materials include absorbent paper, filter paper, cellulose sheet or film, cardboard or similar material. Suitable papers include those available from Whatmann or sold under the trade name Advantech.

The apparatus of either embodiment may be provided in a test kit. The apparatus of the first and second embodiments of the present invention may be provided alone or in combination. Each, or both, may be provided in combination with apparatus for testing for other drugs including other tests for benzodiazepines, amphetamines, cocaine, barbiturates, opiates, tricyclic antidepressants, acetaminophen, propoxyphene and phencyclidine.

Examples of suitable tests can be found in GB2383130 and GB0329503 filed on 19 Dec. 2003 which are incorporated herein by reference.

Examples of the configuration in which the apparatus of the present invention may be provided for use are also described in these documents.

The present invention will now be described by way of example with reference to the accompanying example.

EXAMPLE 1

0.4 g of lacmoid were dissolved in 1000 ml of acetone and buffered with 3.5 ml of concentrated hydrochloric acid. Standard Whatmann No 1 was impregnated by dipping and oven drying. When a standard 250 ml drink having an equivalent gamma-hydroxybutyrate material is applied to the test paper a clear blue colour was noted.

EXAMPLE 2

Apparatus for testing gamma-hydroxybutyrate were produced using a range of visualization reagents. Details can be found in Table 1.

TABLE 1

| Visualisation Reagent | Comment |
| --- | --- |
| Cobalt nitrate | Gamma-hydroxybutyrate gives violet colour. However, the presence of aqueous produces false negative |
| Oxammonium chloride/ Ferric Chloride | Gamma-hydroxybutyrate gives purple colour. However, it is not preferred since it is very difficult to impregnate into paper and sensitivity lost. Some drinks produce false negatives |
| Oxammonium sulphate/ Ferric Chloride | Gamma-hydroxybutyrate gives purple colour. More sensitive than oxammonium chloride. Very difficult to impregnate into paper and sensitivity lost. Many drinks produce false negatives |
| 5% Ferric Chloride | Gamma-hydroxybutyrate gives brown precipitate. Poor sensitivity. Many interfering compounds. Alkaline solutions destroy reaction. |
| Satd. Potassium Dichromate | Gamma-hydroxybutyrate gives an orange to green reaction. Poor sensitivity. Alcohol interferes. |
| Toluene/Cobalt thiocyanate | Gamma-hydroxybutyrate produces blue in organic phase. Poor sensitivity. Not applicable to paper strips. |
| Chromium (VI) Oxide: Sulphuric Acid conc. | Gamma-hydroxybutyrate produces an orange to green reaction. Alcohols interfere. Poor sensitivity. |
| Loane's Reagent based on Lacmoid | Gamma-hydroxybutyrate has excellent detection in most beverages. Very sensitive. |

EXAMPLE 3

The modified Dragendorff Reagent was prepared as follows:

Solution A was prepared by dissolving 6.24 g potassium iodide and 7.0 g sodium bisuphate in 500 ml water.

Solution B was prepared by dissolving 1.8 g bismuth sub.nitrate to 780 ml of methylated spirits. 170 ml concentrated hydrogen chloride is added slowly with stirring until all of the bismuth sub.nitrate has dissolved.

Solution A is added to Solution B with stirring to produce a golden orange/yellow solution. Whatmann paper sheets are then immersed in the solution and then allowed to dry. The presence of secondary amines in the drink will give an instant (i.e. <10 secs) solid orange/red coloration when the drink is brought into contact with the paper.

The invention claimed is:

1. An apparatus for detecting the presence of ketamines or other drugs in a beverage, the apparatus comprising:
   a substrate and
   a modified-Dragendorff Reagent comprising sodium bisulphate;
   wherein the modified-Dragendorff Reagent comprising sodium bisulphate is supported on the substrate.

2. The apparatus according to claim 1, wherein the substrate is selected from absorbent paper, filter paper, cellulose sheet, cellulose film or cardboard.

3. A test kit comprising the apparatus of claim 1.

4. The test kit according to claim 3 additionally comprising a test for other drugs.

5. The test kit of claim 3 additionally comprising instructions for use.

6. The apparatus according to claim 1, wherein the modified-Dragendorff Reagent comprises potassium and bismuth.

7. The apparatus according to claim 1, wherein the modified-Dragendorff Reagent comprises potassium, bismuth, iodine, and sodium bisulphate.

8. The apparatus according to claim 1, wherein the modified-Dragendorff Reagent is formed by mixing potassium iodide, sodium bisulphate, and bismuth nitrate.

9. The apparatus according to claim 1, wherein the modified-Dragendorff Reagent is formed by:
  mixing potassium iodide and sodium bisulphate to form solution A;
  mixing bismuth nitrate, methylated spirits, and hydrogen chloride to form solution B; and
  mixing solution A and solution B to form the modified-Dragendorff Reagent.

10. The apparatus according to claim 1, wherein the sodium bisulphate is present at a concentration sufficient to reduce precipitation of bismuth from the modified-Dragendorff Reagent as compared to a Dragendorff Reagent not containing sodium bisulphate.

11. The apparatus according to claim 1, wherein the modified-Dragendorff Reagent further comprises tartaric acid, oxalic acid, or citric acid.

12. The apparatus according to claim 1, wherein the modified-Dragendorff Reagent is dry on the substrate prior to contact with a beverage.

13. The apparatus according to claim 1, wherein the apparatus is formed by contacting the substrate and aqueous modified-Dragendorff Reagent and subsequently drying the substrate and the modified-Dragendorff Reagent.

14. The apparatus according to claim 1, wherein an orange, pink, orange/pink, or orange/red coloration is formed after contact of the apparatus and a sample containing ketamine.

15. The apparatus according to claim 1, wherein an orange/red coloration is formed after contact of the apparatus and a sample containing a secondary amine compound.

16. The apparatus according to claim 1, wherein an orange/red coloration is formed after contact of the apparatus and a sample containing benzodiazepine.

17. The apparatus according to claim 1, wherein a colorimetric indicator appears in less than 10 seconds after contact of the apparatus and a sample containing ketamine.

18. The kit according to claim 4, wherein the test kit comprises a test for benzodiazepine, amphetamines, cocaine, barbiturates, opiates, tricyclic antidepressants, acetaminophen, propoxyphene, or phencyclidine.

* * * * *